United States Patent [19]

Tatge

[11] Patent Number: 4,817,607
[45] Date of Patent: Apr. 4, 1989

[54] MAGNETIC OSSICULAR REPLACEMENT PROSTHESIS

[75] Inventor: Gary Tatge, Germantown, Tenn.

[73] Assignee: Richards Medical Company, Memphis, Tenn.

[21] Appl. No.: 50,909

[22] Filed: May 15, 1987

Related U.S. Application Data

[63] Continuation-in-part of Ser. No. 837,708, Mar. 7, 1986.

[51] Int. Cl.$^4$ ............................ A61N 1/00; H05G 1/00
[52] U.S. Cl. .................................... 128/419 R; 623/10
[58] Field of Search ............... 128/420.5, 420.6, 1 R, 128/92 C, 419; 623/9, 10, 11, 12

[56] References Cited

U.S. PATENT DOCUMENTS

| | | | |
|---|---|---|---|
| 3,473,170 | 10/1969 | Haase et al. | 128/421 |
| 3,710,399 | 1/1973 | Hurst | 128/421 |
| 3,838,468 | 10/1974 | Armstrong | 128/421 |
| 3,870,832 | 4/1975 | Fredrickson | 128/419 |
| 3,909,852 | 10/1975 | Homsy | 623/10 |
| 4,052,754 | 10/1977 | Homsy | 128/1 R |
| 4,281,419 | 8/1981 | Treace | 623/10 |
| 4,287,616 | 9/1981 | Heimke et al. | 3/1.9 |
| 4,292,693 | 10/1981 | Shea et al. | 623/10 |
| 4,473,909 | 10/1984 | Reck et al. | 623/10 |
| 4,510,627 | 4/1985 | Treace et al. | 128/421 |
| 4,606,329 | 8/1986 | Hough | 128/420.6 |
| 4,628,907 | 12/1986 | Epley | 128/1 R |

OTHER PUBLICATIONS

Richards Medical Co., excerpts from catalog showing ossicular replacement prostheses, p. A87-A44.1.
Emmett, Shea and Moretz, Long-term experience with biocompatible ossicular implants, Otolaryngol-Head and Neck Surgery, vol. 94, No. 5, 1986, p. 611-615.

Primary Examiner—Francis Jaworski
Assistant Examiner—George Manuel
Attorney, Agent, or Firm—Pravel, Gambrell, Hewitt, Kimball & Krieger

[57] ABSTRACT

An ossicular replacement prosthesis containing a magnet in the head of the prosthesis so that when used with a magnetic induction hearing aid having a coil producing a magnetic field, the hearing losses resulting from insertion of the prosthesis and any other remaining hearing losses can be corrected without the difficulties associated with conventional acoustic hearing aids.

12 Claims, 6 Drawing Sheets

MAGNETIC OSSICULAR REPLACEMENT PROSTHESIS

This application is a continuation-in-part of copending application Ser. No. 837,708, filed Mar. 7, 1986.

BACKGROUND OF THE INVENTION

1. Field of the Invention

The present invention relates to hearing aids and to ossicular prostheses, and, more particularly, to a prothesis used in conjunction with a hearing aid using magnetic induction to reproduce sound.

2. Description of the Prior Art

Hearing aids are useful in restoring lost aural perception to those persons having mild to severe loss of hearing. Conventional hearing aids have a microphone, amplifier circuitry, a battery and a speaker. The microphone receives the sound energy and transforms the sound energy into an electrical signal which is then amplified and filtered. This amplified signal is transformed back to acoustic energy by the speaker and transmitted to the person's middle ear for perception of the sound. These hearing aids can be placed behind the ear, with only the receiver being placed inside the ear canal. Alternatively, in-the-ear hearing aids are available which are placed in the outer ear and have portions extending into the ear canal.

There are a number of problems with conventional hearing aids. All conventional hearing aids are visible to some extent and therefore have an undesirable cosmetic appearance. Conventional hearing aids have acoustic feedback problems because sound energy can escape from the ear canal and be detected by the microphone, generating a feedback-related whistle. Additionally, sound reproduction is often lacking in clarity because of distortions generated by standing waves existing in the closed cavity between the hearing aid and the tympanic membrane and poor mechanical reproduction by the speaker.

It has been suggested that a magnetic induction hearing aid would remove many of these problems. A magnet or other item having a magnetic field is placed in the middle ear, either in contact with the tympanic membrane or in contact with other portions of the middle ear. Electrical circuitry and a coil would generate a magnetic field having the same frequency as the external sound. The magnetic field generated by the coil would interact with the field of the magnet and cause the magnet to vibrate at the same frequency as the magnetic field. The vibration of the magnet would then cause the attached portion of the middle ear to vibrate, resulting in a perception of the external sound.

A magnetic induction hearing aid would overcome feedback or distortion problems of conventional hearing aids because there would be no significant air movement in the ear canal, resulting in insufficient energy escaping around the hearing aid to generate a feedback problem. There would be no standing waves generated to cause distortion because there are no appreciable sound waves at all.

Attempts to use magnetic induction hearing aids have been reported. An early attempt placed a coil in conjunction with a small piece of iron on the tympanic membrane, which was excited by an external coil placed over the ear canal. This system did allow the perception of the stimulus, but had the side effect of producing discomfort and pain for the wearer. A later attempt glued a small magnet to the umbo and used an external coil placed over the ear of the wearer to cause the sympathetic vibrations of the magnet. This apparatus required approximately 7.9 ma to produce a 0 db hearing level at 1000 Hz.

In an article entitled *Audition via Electromagnetic Induction,* Arch Otolaryngol 23 (July 1973), Goode et al describe a number of tests. One test attached a magnet to the tympanic membrane and located a coil in the ear canal 3 mm from the magnet. The coil was driven externally by an audiometer. This development required only 0.7 $\mu$a to produce a 0 db hearing level at 1000 Hz. Tests were performed for system fidelity and proved adequate. Another system tested placed the coil over the ear, drove the coil with an audiometer and had a magnet glued to portions of the middle ear, but used larger magnets than in previous tests. One version of this system placed the magnet on a Silverstein malleus clip which was connected in the normal manner. Approximately 0.7 ma was required to produce a 0 db hearing level using these arrangements.

These discussions suggested that the use of electromagnetic induction to produce a hearing aid is possible, but did not teach a way to develop a practical system. The majority of tests used coils placed over the ear or adjacent to the ear. Systems using external coils are not efficient enough for use in conjunction with the low power requirements dictated by hearing aid batteries. Although one test indicated that a coil was placed inside the ear canal, an external amplifier was used to drive the coil. The tests did not result in a practical device or suggest how a totally in-the-ear device could be made.

Further, the magnets described in conjunction with the above-mentioned tests were either glued to portions of the middle ear and removed after short periods of time or were connected to malleus clip and inserted for a longer duration. Neither of these attempts resulted in a magnet that could be implanted for extended periods of time with no danger of rejection by the body, have no movement in relation to the middle ear and yet have as little weight as possible.

In a number of people, portions of the ossicular chain have been damaged due to trauma or other reasons and therefore a hearing loss occurs. One solution to this problem has been the use of ossicular prostheses to replace the damaged portions of the ossicular chain. The prostheses include total ossicular replacement prostheses and partial ossicular replacement protheses depending upon the damage to the individual ossicular chain. In addition, many of the patients with damage to portions of the middle ear also have damage to the sensorineural portions of the ear contained in the cochlea. The placement of a prosthesis allows an individual to regain significant amounts of the hearing that was lost due to the damage to the ossicular chain, but in a majority of cases there is still a residual hearing loss. Correction of the residual hearing loss has typically been performed by using traditional hearing aids which have the problems discussed above. Therefore, although the addition of a prosthesis is a large step in solving a hearing loss developed due to damage of the ossicular chain, conventional hearing aids must still be used to bring hearing levels up to that existing prior to damage to the middle ear.

SUMMARY OF THE INVENTION

The present invention is directed to a magnetic induction, in-the-ear hearing aid where all the elements of the hearing aid are placed within the ear canal and the middle ear. A microphone, amplifying electronics, battery and driving coil are placed within a single housing which is custom molded for each wearer and placed deep within the ear canal.

The amplifier is one of two types, either Class A or Class B, depending on volume levels required. The coils are matched to the particular amplifier type to provide optimal efficiency for a given design. The coil is formed of a number of turns of wire wound over a mumetal core, which is used to increase magnetic field strength. The coil is placed close to the magnet to allow optimal coupling of the magnet's field with the magnetic field produced by the coil.

The magnet is formed of a neodymium-iron material allowing a very high strength magnetic field to be developed by a very small magnet. Since this material corrodes when placed in an animal body, it is coated with a biocompatible material.

If an ossicular replacement prothesis has been inserted in the patient to replace defective portions of the ossicular chain, the magnet can be located in the prosthesis. The magnet is primarily located in the head of the prosthesis with portions of the magnet optionally located in the shaft of the prosthesis if desired. The magnet installed in the prosthesis is preferably formed of samarium cobalt, which has a history of use in the body. Further, the magnet can be coated with a biocompatible polymer as commonly used in implantable medical devices. This magnet is then located in the prosthesis, which is commonly formed of biocompatible polymers, including high-density polyethylene and other porous, biocompatible materials. The location of the magnet in the head of the prosthesis allows the magnet to be placed near the tympanic membrane and in a desirable geometric relationship to the coil in the hearing aid. Alternatively, the magnet can form the entire head of the prosthesis with the shaft attached to the magnet to form the prosthesis. The hearing aid is then used to induce further movement into the prosthesis to supply motion to compensate for the hearing loss due to both the use of the prosthesis and any sensorineural damage component present in the individual.

BRIEF DESCRIPTION OF THE DRAWINGS

A better understanding of the invention can be obtained when the detailed exemplary embodiment set forth below is considered in conjunction with the following drawings, in which.

DETAILED DESCRIPTION OF EXEMPLARY EMBODIMENTS

Figure 1:
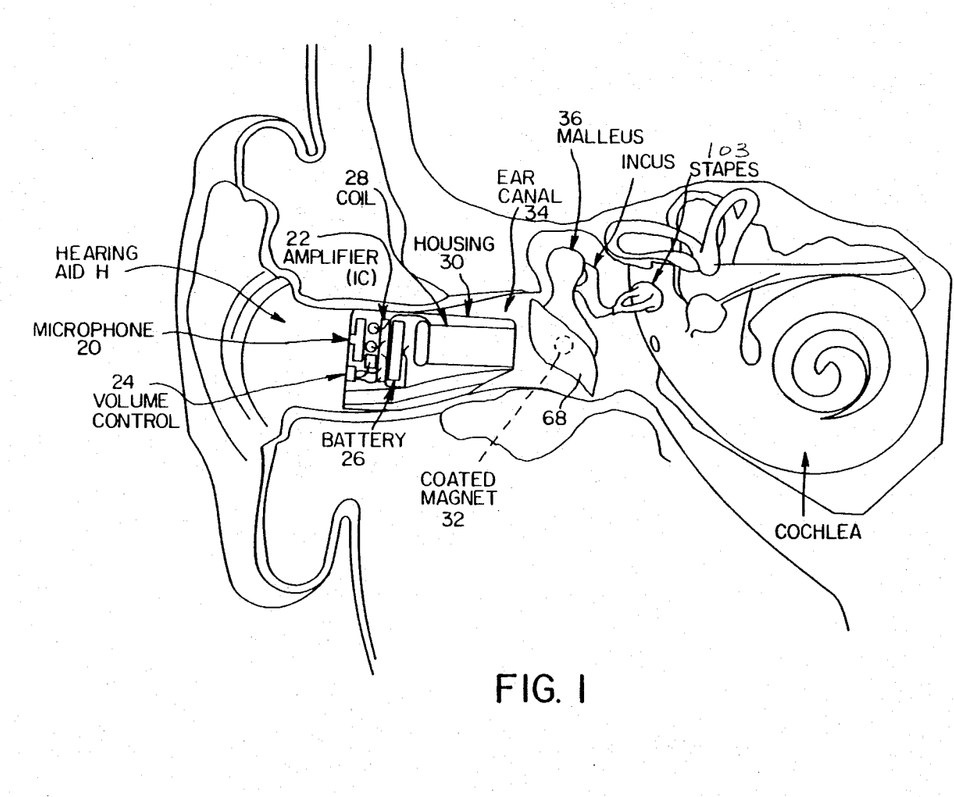
FIG. 1 is a cross-sectional view of a human ear with a magnetic induction hearing aid according to the present invention placed in the ear canal.

Referring to FIG. 1, the letter H refers generally to a hearing aid according to the present invention and is shown installed in an ear canal 34. The hearing aid H has a housing 30 enclosing a microphone 20, an amplifier 22, a volume control 24, a battery 26 and a coil 28. The hearing aid H is located deep in the ear canal 34 so that the coil 28 is located near a coated magnet 32, with 2.5 mm being a desirable distance for this separation. This distance is sufficiently close to reduce the inverse relationship of distance to magnetic field strength and yet is sufficiently far that the hearing aid H can be inserted by the wearer with minimal difficulty and not be in danger of contacting the tympanic membrane 68.

The installation of the hearing aid H deep within the ear canal 34 as shown in FIG. 1 eliminates any negative cosmetic effects of a hearing aid because the hearing aid H is practically undetectable. A conventional hearing aid cannot be inserted this deep in the ear canal 34 because of the standing wave and feedback problems discussed above. These problems do not occur in a magnetic induction hearing aid and therefore this deep placement is possible.

Volume adjustment and battery replacement is accomplished by removing hearing aid H from the ear canal 34, appropriately adjusting the volume control 24 or replacing the battery 26 and reinserting the hearing aid H into the position shown in FIG. 1.

The housing 30 is custom molded to each wearer's ear canal 34. This is necessary because each wearer has a differently sized and shaped ear canal. The hearing aid H must be sufficiently close to the magnet 32 for proper operation and the hearing aid H must be sufficiently tight within the ear canal 34 to remain in place during normal use.

Figure 2:
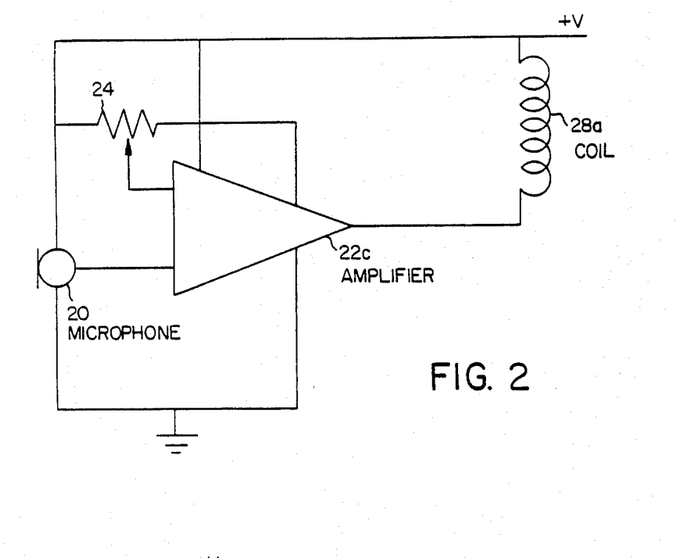
FIG. 2 is an electrical schematic diagram of one embodiment o a circuit utilizing a Class A amplifier designed according to the present invention.

A class A amplifier design is shown in FIG. 2. The microphone 20 is a standard electret microphone as conventionally used in hearing aids. The amplifier 22c is class A design that is standard in hearing aid applications. This amplifier is specifically designed for low voltage operation in conjunction with a single 1.3 volt battery. The volume control 24 is connected to vary the gain of the amplifier 22c and thereby change the output signal level applied to the coil 28a. The coil 28a is designed for use with the class A amplifier 22c.

Figure 8A:
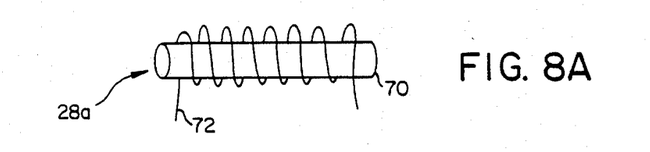
FIGS. 8a, 8b and 8c are schematic illustrations of coils formed according to the present invention.

Each amplifier used in hearing aids has a recommended output load impedance which is normally deemed to be the speaker or receiver impedance. For optimum performance of the hearing aid H, the coil 28a should be designed to match this characteristic desired impedance across as wide a frequency band as possible. The coil 28a is a double-ended coil designed to be connected to the battery 26 and to the output of the amplifier 22c. The coil 28a is formed by winding the appropriate number of turns of wire 72 (FIG. 8a) about a high permeability core 70. Preferably, the core 70 is comprised of mumetal to increase the magnetic field strength at the ends of the coil. The maximum coil size is preferably approximately 9 mm long and 4 mm in diameter. This size limitation is used in conjunction with the optimum coil impedance in determining the number of turns of wire 72 and the gauge of the wire 72 to produce a coil of the allowed size having the desired impedance.

Figure 3:
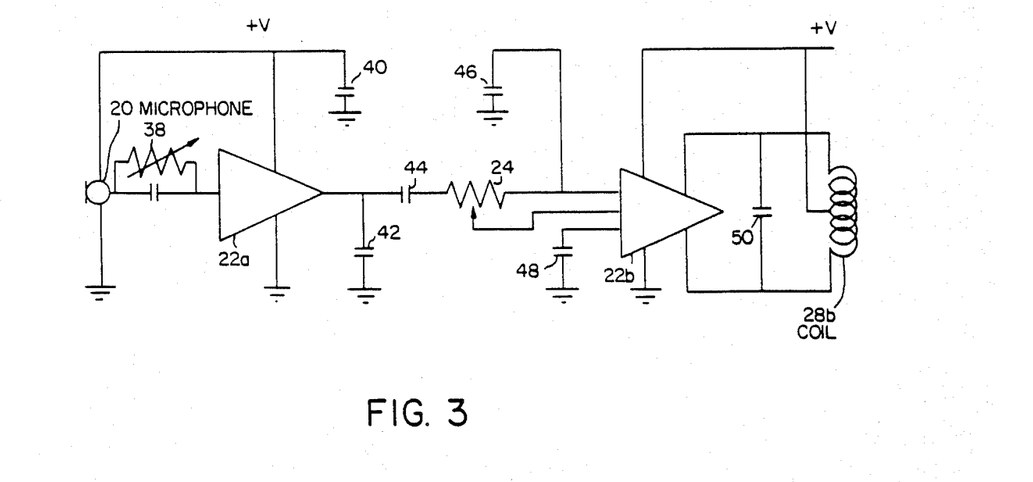
FIG. 3 is an electrical schematic diagram of a second embodiment of a circuit utilizing a Class B amplifier designed according to the present invention.

The class A amplifier 22c is used in situations where the wearer has only a mild to moderate loss of hearing. The class A design is used in the mild loss case because the power consumption of the class A amplifier 22c is lower, but the maximum output is also lower, necessitating a higher performance or class B design for high power needs.

Where the wearer has a more severe hearing loss requiring greater amplification of the sound signal, what is known as a class B amplifier design as shown in FIG. 3 is used. A class B amplifier 22b is used in the higher volume, higher amplification situations because it has a power output level higher than that of the class A amplifier 22c. The trade off for this efficiency is reduced battery life because of the higher current draw of the class B amplifier design.

Figure 8B:
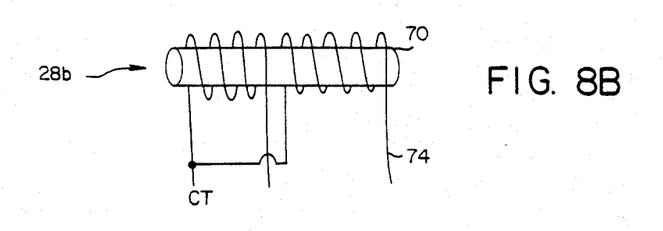
Figure 8C:
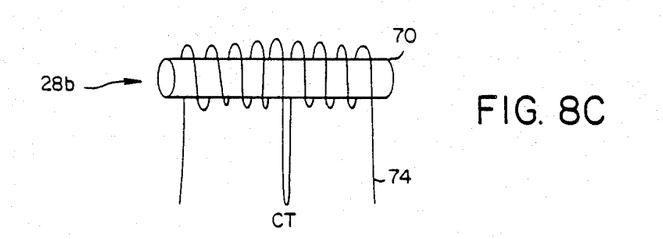

The microphone 20 is connected to a preamplifier stage 22a through an impedance matching and filter stage 38. The class A preamplifier 22a provides a fixed amount of gain and produces an output signal which is transmitted to filter capacitors 42 and 44 and the volume control 24. Appropriately adjusting the volume control 24 changes the output voltage of the class B output amplifier 22b which in turn drives coil 28b. As in the class A amplifier 22c, the class B output amplifier 22b has an optimal load impedance resistance which is specified by the manufacturer. The coil 28b is designed to have an impedance which matches this optimal impedance over as broad a frequency band as is necessary for the given application. The coil 28b is designed with a center tap (FIGS. 8b and 8c) to allow use with the class B amplifier 22b. An appropriate number of turns of the appropriate gauge wire 74 are wound around the mu-metal core 70 or other high permeability material and connected as required to the amplifier 22b. The class B amplifier 22b produces greater power because of its class B design and its push-pull operation, enabling the coil 28b to produce larger magnetic field densities and thereby move the magnet 32 a greater distance.

Figure 6:
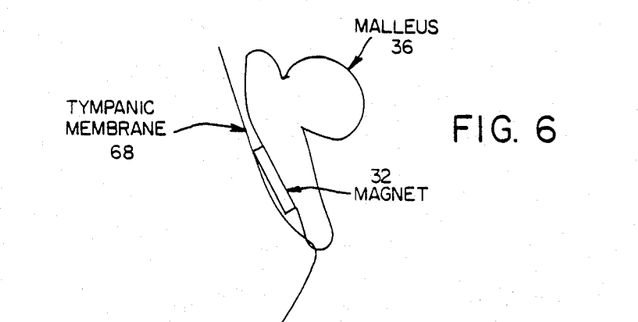
FIG. 6 is a partial cross-sectional view of a middle ear showing an magnet implanted according to the present invention.
Figure 7:
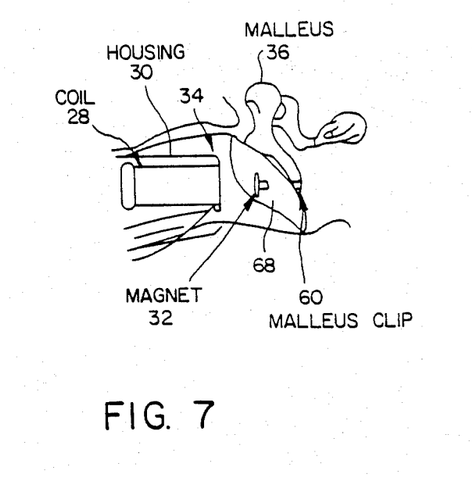
FIG. 7 is a cross-sectional view of an eardrum or tympanic membrane and malleus in which a magnet mounted to a malleus clip is connected to the malleus.

The coil 28 produces a magnetic field varying at the frequency of the sound waves received by the microphone 20. The coil's magnetic field then interacts with the magnet 32. A sympathetic vibration of the magnet 32 occurs at the frequency of the sound waves. This mechanical vibration of the magnet 32 is then translated into movement of either the malleus 36 if the magnet 32 is attached to a malleus clip 60 (FIG. 7) or to vibration of the malleus 36 and the tympanic membrane 68 if the magnet 32 is inserted between the malleus 36 and the tympanic membrane 68 as shown in FIG. 6.

It is desirable that the coil 28 be placed in close proximity to the magnet 32 because a magnetic field decreases with strength according to the inverse cube law. Therefore, the coil's magnetic field effecting and interacting with the magnet 32 is radically diminished as the separation distance increases. This diminishing interaction directly effects the efficiency of the hearing aid H and therefore a minimum gap is desirable.

If the magnet 32 is implanted behind the tympanic membrane 68, the magnet 32 can move by either of two actions. The first movement is a piston-type action perpendicular to the plane of the membrane 68. The second action of the magnet 32 is a rocking action about a horizontal axis of the magnet 32. This rocking does cause the tympanic membrane 68 and the malleus 36 to vibrate, creating a sensation of sound. The rocking action is preferable because there is better magnetic coupling between the magnet 32 and the coil field, which increases effective acoustic gain and thereby system efficiency.

The mass of the magnet 32 must be kept at a minimum to further increase the efficiency of the design so that the coil's magnetic field does not have to oscillate a large mass and therefore require additional energy transfer between the coil 28 and the magnet 32. But the magnet 32 must also be high strength so that the two interacting magnetic fields, the coil field and the magnet field, are sufficiently strong to create a sufficient amount of coupling between the two fields. For this reason it is preferable that the magnet 32 be formed from the neodymium-iron which has an extremely high field strength for a given magnet size.

Because the magnet 32 is to be inserted in the human body it is necessary that the magnet 32 or magnet assembly be biocompatible and not corrode or cause adverse tissue reaction when placed in the body. It is also desirable that the magnet become firmly and permanently attached to the desired portions of the middle ear.

The preferred neodymium-iron magnet, in and of itself, does not meet these requirements. It corrodes when placed in the body and therefore is not suitable in its uncoated state for long-term placement or installation. Therefore, for biocompatibility the magnet 32 must be coated and sealed with a biocompatible material. There are two alternative versions of the coated magnet 32, one for use with the malleous clip 60 and the other for direct implantation between the tympanic membrane 68 and the malleous 36.

Figure 4:
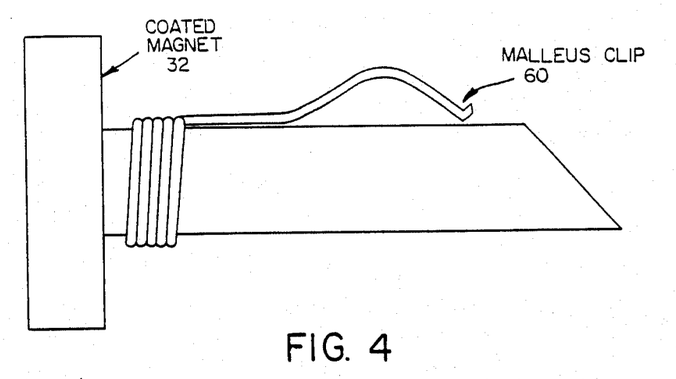
FIG. 4 is a side view of a malleus clip having a magnet mounted thereon.
Figure 5A:
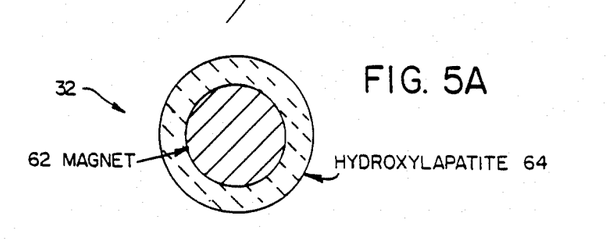
FIGS. 5a, 5b, 5c and 5d are, respectively, cross-sectional top and side views of a magnets formed according to the present invention.
Figure 5B:
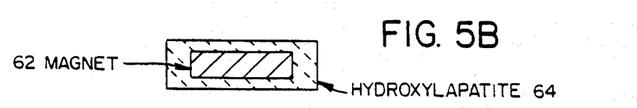
Figure 5C:
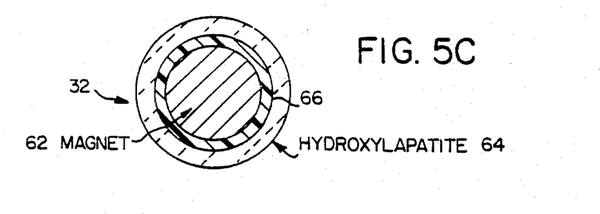
Figure 5D:
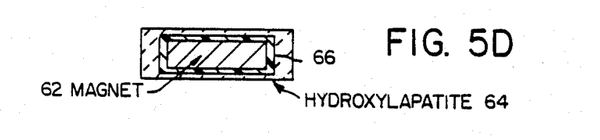

The magnet 32 that is attached to the malleous clip 60 (FIG. 4) need only be biocompatible such that it does not produce an infection and does not corrode. For this use, a coating of the magnet with biocompatible materials such as gold or other nonresorbable, biocompatible material such as various commonly available polymers is necessary. No actual mechanical bonding between the magnet 32 and portions of the middle ear is necessary because the malleous clip 60 provides the connection with the malleous 36 and the magnet 32 is firmly mounted on the malleous clip 60.

For the embodiment of the magnet 32 to be used for direct implantation between the tympanic membrane 68 and the malleous 36, different criteria must be considered. It is highly desirable that this magnet 32 be coated with a bioactive material which will form a permanent bond with the middle ear. To this end it is preferable that the magnet 62 (FIGS. 5a, 5b, 5c, 5d) be coated with hydroxyapatite 64. Hydroxyapatite is a calcium phosphate material which has a particular crystal structure which resists biodeterioration and has an outer surface that easily adheres to tissue that is generated by the adjacent body portion.

Hydroxyapatite is preferred as the material that is useable as an outer coating material, but other non-resorbable bioactive materials could be used. Hydroxyapatite is referred to in this specification because it is the currently preferred material and these references to hydroxyapatite are intended to include other similar materials. Coating the magnet 62 with hydroxyapatite 64 and placing the coated magnet 32 between the tympanic membrane 68 and the malleous 36 results in the magnet 32 becoming part of the middle ear after a period of time due growth of middle ear tissue and its adherance to the hydroxyapatite coating 64.

A coating of hydroxyapatite 64 over a bare magnet 62 might possibly be satisfactory if the magnet were sealed from surrounding body fluids. However, because a neodymium-iron magnet is highly corrodable in an animal body and a complete seal is difficult to achieve, the magnet 62 first receive a precoating 66 prior to the final coating of hydroxyapatite 64. This precoating 66 is used to seal the magnet 62 from the bodily environment and therefore resist corrosion. The sealant can be a biocompatible material such as gold or other biocompatible polymers as are used in implantable medical devices. The precoated magnet is then coated with the hydroxyapatite 64 or other nonresorbable bioactive materials with similar properties.

There are several different processes that could be used for applying the hydroxyapatite coating. The first process is an ion implantation or sputtering technique wherein the target magnet is placed inside a vacuum chamber and positioned near a hydroxyapatite source. The hydroxyapatite source is then bombarded by an electron beam source from an ion accelerator so that the hydroxyapatite atoms are stripped from the source material and attracted to the target material due to electrostatic forces. Alternatively, a hydroxyapatite plasma can be produced by a radio frequency power source and directed toward the target material. The charged hydroxyapatite atoms are then driven into the magnet 62 or the precoat 66 by means of an accelerated argon ion beam. This firmly implants the hydroxyapatite atoms into the magnet 62 or precoat 66 forming a firm bond between the two layers. This process is continued until a sufficient hydroxyapatite coating thickness is produced, preferably about one micron.

The ion implantation process is a low temperature process which allows the magnet 62 to retain its magnetism. If the magnet 62 is subjected to a sufficiently high temperature, it loses its magnetism and therefore is rendered unusable. For this reason, the target must be kept at a low temperature which is capable of being done in the ion implantation or sputtering technique.

A low temperature process is also important so that the hydroxyapatite source material retains its preferred hydroxyapatite structure. If the materials forming the hydroxyapatite are elevated to a sufficiently high temperature, the hydroxyapatite converts to tricalciumphosphate which is a bioresorbable material and is not satisfactory for coating the magnet 62. This is because the material is resorbed by the body and would eventually disappear from the magnet 62, leaving the magnet 62 uncoated and not bonded as desired. Therefore the low temperature ion implantation technique allows the hydroxyapatite 64 to keep its structure after being sputtered to the target magnet.

A second process for coating the precoated magnet is a plasma spraying technique. In this process the hydroxyapatite 64 is in the form of a powder and is fed through an argon plasma which melts the hydroxyapatite powder which is then fired onto the surface of the target magnet. The hydroxyapatite 64 then cools down, solidifies and is bonded to the precoating material 66. In this process it is possible to keep the substrate or target material temperature sufficiently low so as not to demagnetize the magnet 62.

A third process for applying the hydroxyapatite coating material involves placing the hydroxyapatite material on the surface of the polymer used as the precoat 66 before the polymer precoating material is fully solidified. When the biocompatible precoating polymer material 66 is applied to the magnet 62 in a molten form there is an interval wherein the precoating material 66 is sufficiently adhered to the magnet 62 and yet is not completely solidified. During this tacky or partially fluid state, the hydroxyapatite material is introduced onto the magnet assembly and physically pressed into the precoating material 66, therefore bonding with the precoating material 66 which then completes its hardening process. In this way, the hydroxyapatite material 64 has fully interlaced with the precoating polymer 66 which is firmly attached and sealing the magnet 62. An intermediate biocompatible coating attached to the underlying precoating material 66 can also be used to bond the hydroxyapatite 64 to the magnet 62.

Figure 9A:
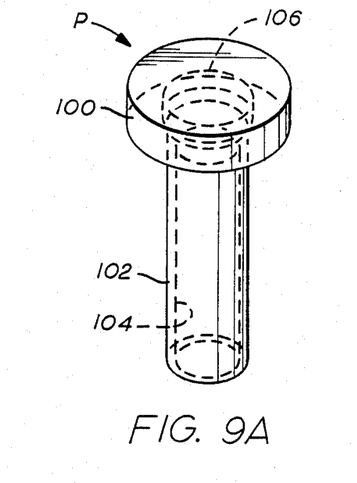
FIGS. 9a-9j are perspective views of protheses formed according to the present invention.
Figure 9B:
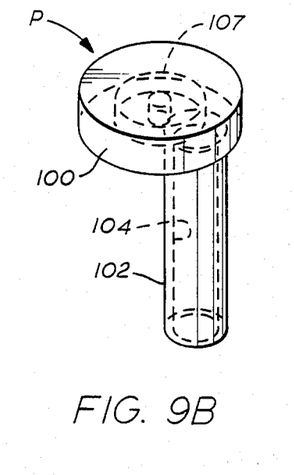
Figure 9C:
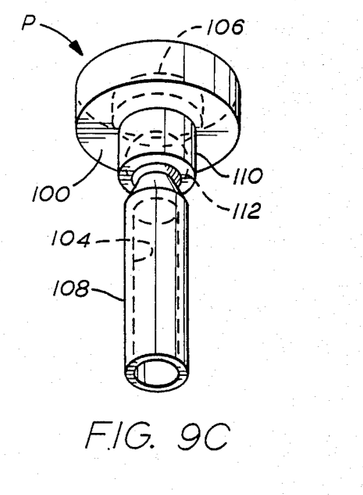
Figure 9D:
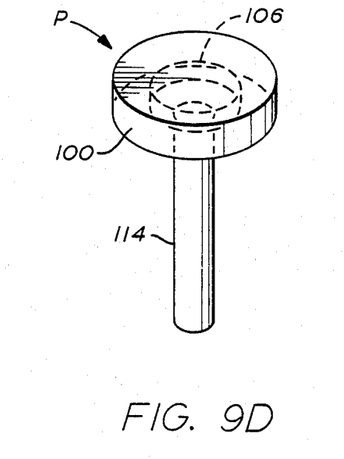
Figure 9E:
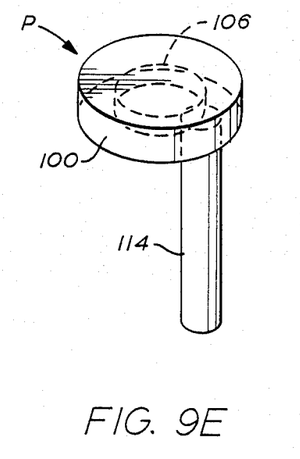
Figure 9F:
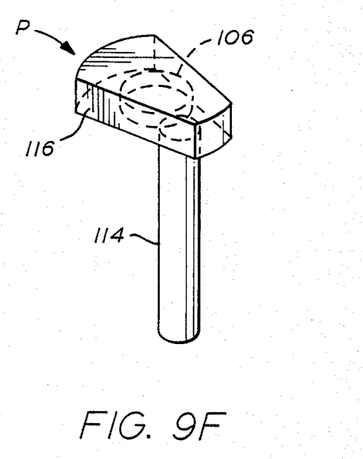

Referring to FIGS. 9a-9j, the letter P generally refers to a prosthesis according to the present invention containing a magnet. FIGS. 9a-9c show partial ossicular replacement prostheses, while FIGS. 9d-9j show total ossicular replacement prostheses.

The prothesis P (FIG. 9a) generally contains a head 100 and a shaft 102. The head 100 is located adjacent to the tympanic membrane 68 to receive the sound waves from the outer ear, which are transmitted to the inner ear by the prosthesis. The shaft 102 of a partial prosthesis contains an internal cavity 104 which is coaxial with the shaft 102 for interlocking with the stapes 103. The shaft 102 is connected at one end to the head 100 and is connected to the stapes 103 at the other end.

The magnet 106 is preferably located inside the head 100 of the prosthesis P but can additionally be located in the shaft 102. The location of the magnet 106 in the head 100 provides optimal coupling of the magnetic field produced by the magnet 106 and the magnetic field produced by the coil 28 of the hearing aid H. In the preferred embodiment, the magnet 106 is a samarium cobalt magnet having a diameter of approximately 0.10" and is approximately 0.034" thick. Alternate magnet materials including neodymium-iron can be used to form the magnet 106. The magnet 106 can be coated with biocompatible polymers to increase its corrosion resistance and its biocompatibility. The prothesis P is preferably formed of a porous biocompatible material, but can be formed of other materials known in the art.

In the prosthesis P of FIG. 9a, the shaft 102 is coaxial with the head 100. In FIG. 9b, the shaft 102 has an axis which is co-linear with the axis of the head 100 but is offset from the head axis. Also shown in FIG. 9b is a magnet 107 which has a toroidal configuration. The use of the toroidal form for the magnet allows a reduction in weight of the magnet without a significant loss in the magnetic field of the magnet 107. The weight of the magnet and the entire prostheis has an effect on the hearing aid. The heavier the prosthesis P, whose primary weight component is the magnet, the better the coupling between the two magnetic fields and therefore the longer the hearing aid battery life, but also the greater the reduction in the high frequency response of the unit. A heavier prosthesis has a poorer high frequency response because of inertial problems due to the weight of the prosthesis. The lighter the prosthesis, primarily achieved by using a lighter magnet, the better the aural frequency response of the hearing aid but the lower the hearing aid battery life because of the reduced magnetic coupling between the two magnetic fields. The preferred embodiment uses a magnet weighing approximately 35 milligrams and prosthesis weighing approximately 43 milligrams.

The head 100 can additionally be attached to a shaft 108 (FIG. 9c) via a ball 112 and socket 110 joint to allow improved positioning of the prosthesis within the middle ear.

Figure 9G:
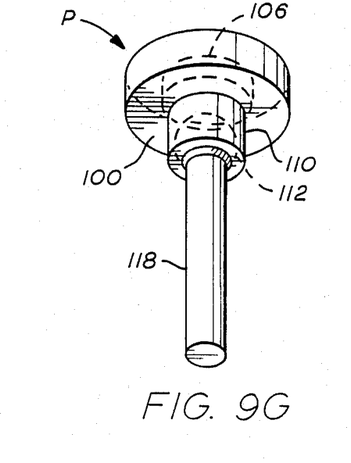
Figure 9H:
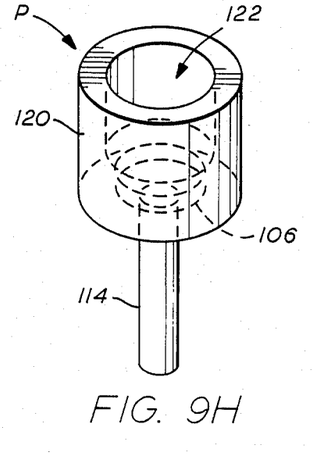

The prosthesis P can also be formed from a head 100 and a shaft 114 which is longer than the partial prosthesis shaft 102 and does not contain a central cavity. The longer shaft 114 is necessitated in a total ossicular replacement prosthesis because a portion of or the entire stapes 103 is damaged and missing when a total prosthesis is necessitated. The total prosthesis can have the shaft centered (FIG. 9d), offset (FIG. 9e), or pivoted (FIG. 9g).

Figure 9I:
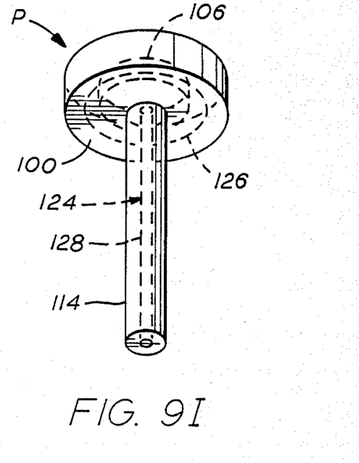
Figure 9J:
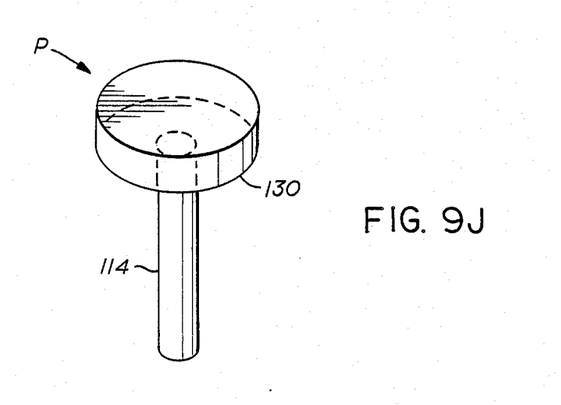

Alternate versions of a total ossicular replacement prosthesis include versions having non-cylindrical heads 116 (FIG. 9f), prostheses having cupped heads 120 (FIG. 9h) and prostheses having internal cores (FIG. 9i). The cupped head 120 contains a cavity or cup 122 in which cartilage is inserted to allow easier placement of the prosthesis by the surgeon.

The shaft 114 and head 100 of the prosthesis P can also contain a core 124. The core 124 preferably includes an enlarged head 126 located in the prosthesis head 100 and a core shaft 128 located substantially coaxial with the prosthesis shaft 114. The core head 126 is preferably substantially concentric with the prosthesis head 100 and is substantially flat. The prosthesis shaft 114 and the core shaft 128 are made of permanently bendable biocompatible materials such as stainless steel so that the shaft 114 can be bent to better conform with or be implanted in the middle ear.

As an alternative to having the magnet 106 located inside the head 100, the magnet 130 (FIG. 9j) can form the entire head of the prosthesis P. This embodiment allows maximum magnet size for a given head size. The magnet 130 can be coated with biocompatible polymers to increase its corrosion resistance and its biocompatibility. The shaft 114 is attached to the magnet 130 and can be formed of porous polymers, hydroxyapatite or other materials known in the art.

The use of the magnet in the prosthesis P allows additional vibration to be transmitted to the cochlea to compensate for hearing loss due to the placement of the prosthesis and due to any damage which has occurred to the cochlea. In this manner an individual having a prosthesis inserted can develop normal hearing levels in an injured ear without the need for using a conventional hearing aid and the problems associated therewith. The inclusion of the magnet in the prosthesis allows the magnet shape and location to be optimized for best coupling with the magnetic field from the hearing aid, for improved efficiency and longer battery life.

The foregoing disclosure and description of the invention are illustrative and explanatory of the invention, and various changes in the size, shape and materials, as well as in the details of the illustrated construction and process may be made without departing from the spirit of the invention, all of which are contemplated as falling within the scope of the appended claims.

I claim:

1. A middle ear ossicular replacement prosthesis for replacing at least a portion of the ossicular chain by making contact with two separated locations in the middle ear and for use with a hearing aid producing a magnetic field corresponding to sound waves received by the wearer, comprising:
   a head portion adapted for contacting the tympanic membrane, said head portion including a magnet; and
   a shaft portion adapted to extend from said head portion to a location in the middle ear,
   wherein said head portion and said shaft portion are adapted to transmit to the inner ear the acoustically induced vibrations of the tympanic membrane received by said head portion and the magnetically induced vibrations developed by the coupling of the magnetic field produced by said magnet and the magnetic field produced by the hearing aid.

2. The prosthesis of claim 1, further comprising:
   a pivotable joint connecting said head portion to said shaft portion.

3. The prosthesis of claim 1, wherein said shaft portion includes a magnet.

4. The prosthesis of claim 1, wherein said shaft portion is coaxial with said head portion.

5. The prosthesis of claim 1, wherein said shaft portion axis is parallel with the axis of said head portion.

6. The prosthesis of claim 1, wherein said shaft portion is hollow.

7. The prosthesis of claim 1, wherein said head portion is generally cylindrical.

8. The prosthesis of claim 1, wherein said magnet is generally cylindrical.

9. The prosthesis of claim 1, wherein said magnet is generally toroidal.

10. The prosthesis of claim 1, wherein said shaft portion and said head portion include a core encased within said shaft portion and said head portion, said core including an elongated core shaft aligned substantially concentric within said shaft portion and further including a first end forming an enlarged and substantially flat head positioned within and substantially concentric within said head portion, said shaft portion and said core being permanently bendable to allow said prosthesis to be permanently bent to a specific shape during implantation thereof to conform to the person's middle ear structure, said core being stationary with respect to said head portion and said shaft portion.

11. The prosthesis of claim 1, wherein said head portion is a magnet.

12. The prosthesis of claim 11, wherein said magnet is coated with a bicompatible material.

* * * * *